United States Patent [19]

Ghadiali

[11] Patent Number: 4,834,082
[45] Date of Patent: May 30, 1989

[54] ARM SLING FOR STROKE PATIENTS

[76] Inventor: Nafisa Z. Ghadiali, 2769 Seabreeze Dr., St. Petersburg, Fla. 33707

[21] Appl. No.: 188,954
[22] Filed: May 2, 1988
[51] Int. Cl.⁴ .............................................. A61F 5/40
[52] U.S. Cl. .................................................... 128/94
[58] Field of Search ...................... 128/94, 87 R, 89 R, 128/77

[56] References Cited

U.S. PATENT DOCUMENTS

| 980,464 | 1/1911 | Wermuth | 128/94 |
| 982,376 | 1/1911 | MacFarlane | 128/94 |
| 1,304,153 | 5/1919 | Bugge | 128/94 |
| 3,103,216 | 9/1963 | Scott | 128/94 |
| 4,232,664 | 11/1980 | Blatt | 128/94 |
| 4,355,635 | 10/1982 | Bihl et al. | 128/94 |
| 4,437,459 | 3/1984 | Slavetskas | 128/94 |
| 4,480,637 | 11/1984 | Florek | 128/94 |
| 4,564,008 | 1/1986 | Donahoo | 128/94 |
| 4,622,961 | 11/1986 | Christensen | 128/94 |
| 4,625,719 | 12/1986 | Chambers | 128/94 |

Primary Examiner—Robert A. Hafer
Assistant Examiner—Michael Brown

[57] ABSTRACT

An arm sling for stroke patients that has of a large trough, to fully support the entire forearm, elastic straps to provide quick stretch facilitation, and a weight distribution ring device that transfers the weight away from the neck and towards the back, allowing the patient to stand up erectly, in a therapeutically advantageous manner.

3 Claims, 4 Drawing Sheets

ARM SLING FOR STROKE PATIENTS

BACKGROUND OF THE INVENTION

This particular Arm Sling is for patients who have suffered upper motor neuron or cerebral vascular accident, resulting in a stroke. Symptoms of a stroke are lack of motor control, decreased sensation throughout the affected half side of the body, cognitive difficulties, and motor perceptual deficits such as memory deficits, lack of awareness, depth perception and distractibility.

One sided paralysis, commonly known as hemiplegia, poses several problems, one of which is a subluxation (mild dislocation) of the shoulder. This is due to weakness in the shoulder girdle musculatures in its inability to keep the head of the humerus in its glenoid fossa (ball and socket joint).

Another problem is edema or swelling at the distal part of the paralyzed arm, which is the wrist and hand, including fingers. Also, due to lack of sensation, the patient is unaware of the limbs, and therefore, not cognizant of its position. Hence, it is imperative to have a proper fitting, comfortable, less binding sling, with a therapeutic value to it.

PRIOR ART

The hemi sling in U.S. Pat. No. 4,437,459 to Slavetskas is made of two parts, and does not have a fully supporting trough. Resilient sling in U.S. Pat. No. 4,327,909 to Neufeld is designed for orthopedic and not for neurological patients. Hemi Arm Sling in U.S. Pat. No. 4,598,703 to Lindemann, provides support to the humerus and does not provide full support to the paralyzed arm and forearm, hence vulnerable to additional trauma and swelling due to gravity.

OBJECTA AND ADVANTAGES

It is an object of this invention to provide an Arm sling which supports the entire arm of the patient in a large, comfortable trough. Due to lack of motor control, lack of sensation and cognitive difficulties, patients are unable to handle a two piece trough. A single full length trough allows cradling of the arm and positioning of the arm in the trough, in supination and in external rotation, which is the more desirable position since spasticity or exaggerated tone exist in certain muscle groups.

It is another object of this invention to have a Arm Sling that is adjustable, allowing the distal part (hand) to be higher than the proximal (elbow). It is this combination of a large trough and adjustable straps that results in a reduction in swelling. Because of the easy adjustability, the forearm can be positioned to various heights, thereby decreasing swelling. This is accomplished by a sling with elastic straps with a long Velcro to allow maximum flexibility and adjustability in the patient, right from the acute phase to the rehabilitative phase in therapy.

Another object of the invention is to promote facilitation of the paralyzed muscles and therefore better therapeutic advantage by use of muscle stretch when the Arm Sling is worn. Stretch is a therapeutic tool used by therapists to facilitate movements in paralyzed muscles of CVA patients. It acts through the muscle spindles for muscle activation. A quick stretch is facilitory for movement to the muscles stretched through the primary endings of the muscle spindles. This is the basis for use of the elastic straps. The Arm Sling is designed to give facilitation to the triceps.

During ambulation, the resilient elastic straps promote a therapeutic advantage to the patient. When the patient is walking, the motion by the elastic strap provides quick stretch to the triceps as it snaps back. As a result of the action of the elastic straps, the pushing of the arm into increased flexion facilitates elbow extension. Thus the elastic straps allow quick stretch.

Another object of this invention is to provide an Arm Sling which provides proper weight distribution of the affected arm over the shoulder and does not have the weight of the affected arm supported by the neck. The distribution of the weight of the arm is typically over the neck of the patient resulting in poor posture and difficulty in ambulation. With other slings, the poor posture from neck flexion diminishes the visual field of the patient, thus, he is forced to look in a downward manner, resulting in a safety problem. The difficulty in ambulation results because he is unable to extend the neck, and since an extension of the neck facilitates extensors of the legs, which is important for proper ambulation, the patient experiences a decreased tolerance for ambulation.

The present invention transfers the weight to the shoulder girdle. This is done by three straps, one anterior, extending from the elbow side, one posterior strap from the back of the trough near the forearm, connected near the medial border of the affected scapula. The third strap is taken underneath the axilla of the unaffected arm and through both the D Rings.

The elastic straps are individually adjustable to custom fit the patient, emphasize proper weight distribution and for comfort. The Arm Sling also has convenient features such as ease of washing, ease of wearing, it can be worn on either the left or right side. The tension distribution ring distributes the weight of the affected arm.

DRAWING FIGURES

FIG. 1 shows the trough of the Arm Sling.
FIG. 2 shows the three strap device.
FIG. 3 shows a patient wearing the invention with the front view.
FIG. 4 shows a patient wearing the invention with the rear view.

Drawing Reference Numerals

50 Trough
60 Three Strap Device
70 Complete Arm Sling
2,4,6,8 Short Elastic Stubs
0,12,14,16 D Rings
11 Trough Material
18, 20 Elastic Straps, Equal Length
22 Elastic Strap, Longer Length
24,26,28 Hook Velcro
30,32,34 Loop Velcro
36 Distribution O Ring

CONSTRUCTION OF THE INVENTION

Referring to the drawings:
FIG. 1 shows the complete trough, 50, of the invention. The said trough comprises a piece of soft, durable material, 11, preferably cotton, which is sewn together in the manner shown, with one end closed, and the other end open. The said trough is large enough to completely support the forearm, elbow and distal interphalangeal joints of the fingers of the patient. Attached to the said trough are short stubs, 2, 4, 6, 8, made of elastic strap material, to hold the D rings, 10, 12, 14, 16.

FIG. 2 shows the three elastic strap device, 60, comprising of straps, 18, 20, 22, all connected to a tension distribution O ring, 36. Each of the straps are provided with a Velcro type hook portion, 24, 26, 28, and a loop portion, 30, 32, 34, as a way to fasten the straps. Of course, the means used for fastening may be different so long as the purpose of ease of operation and adjustability can be achieved, therefore, the means shown are illustrative only, and not limited to the ones shown.

OPERATION OF THE INVENTION

Figure 1:
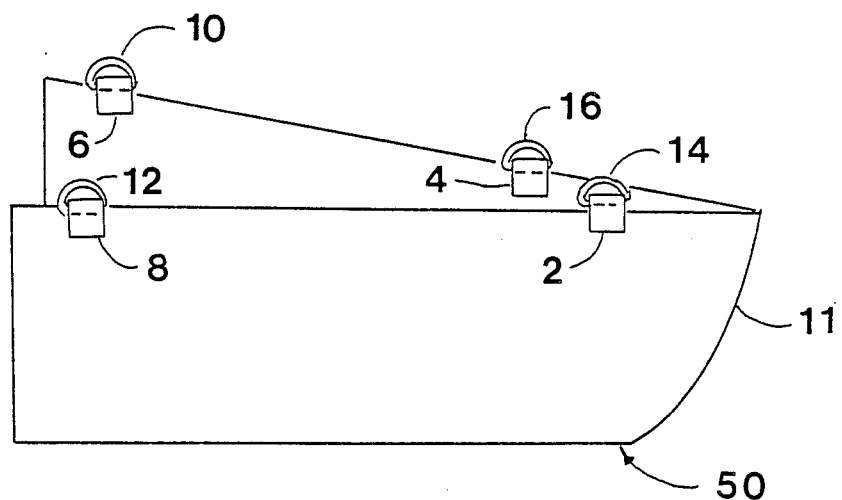
Figure 2:
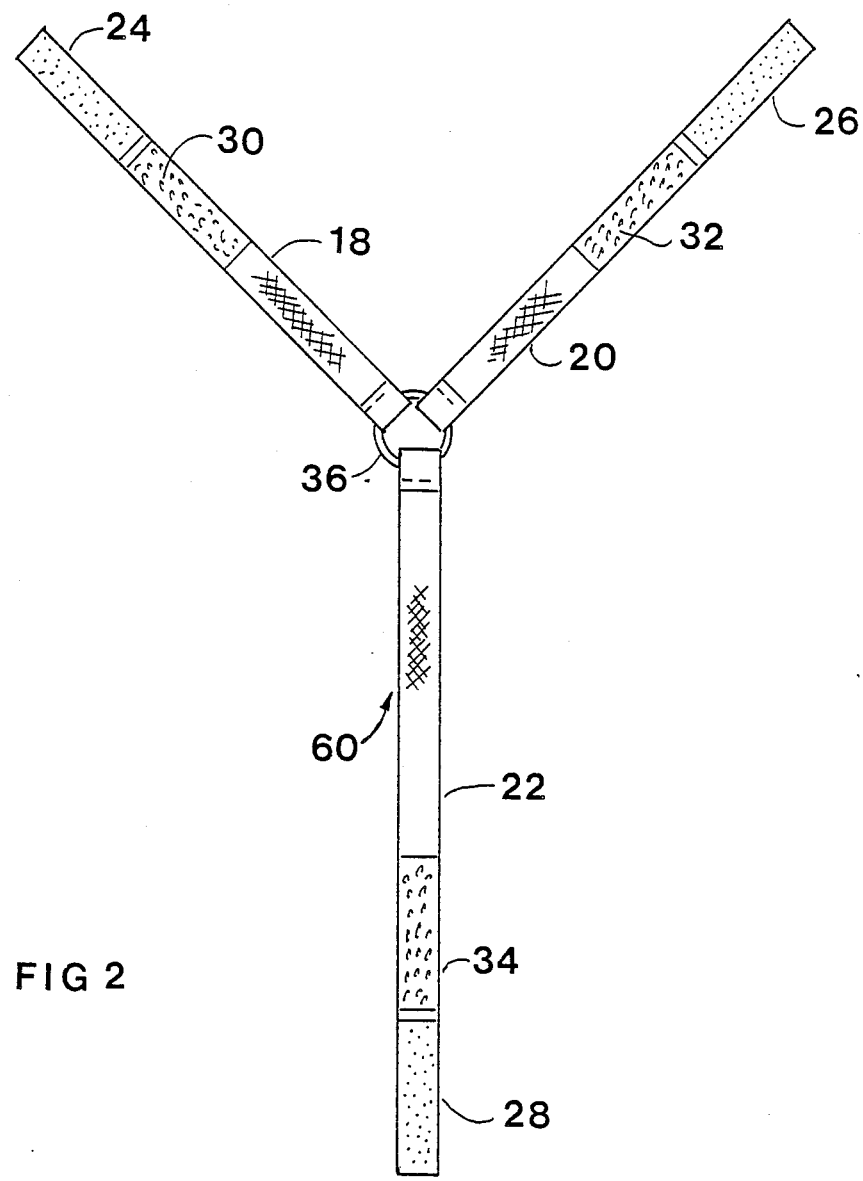
Figure 3:
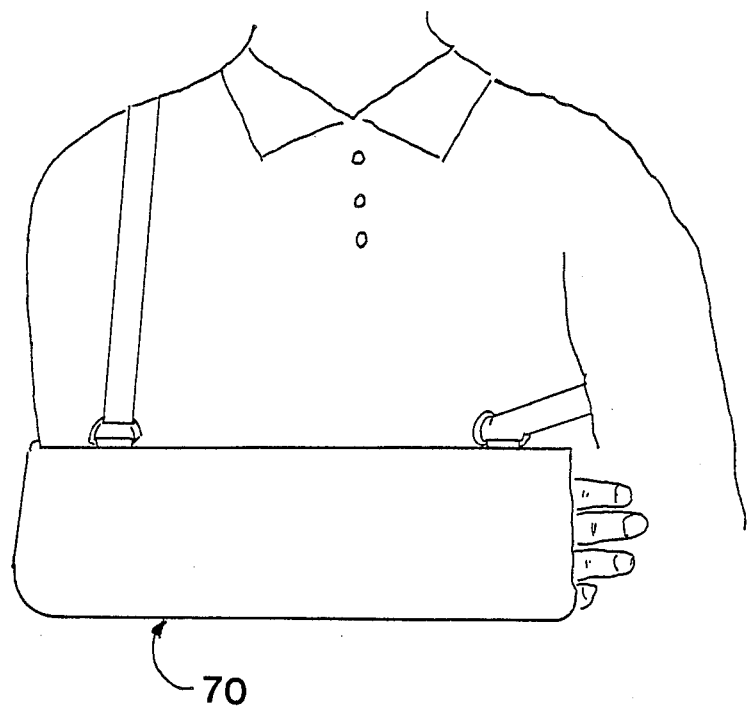
FIG. 3 shows the Arm sling as worn by a patient and seen from the front. The Arm Sling 70, is manufactured so that one size would fit universally, thus reducing the need for several sizes.
Figure 4:
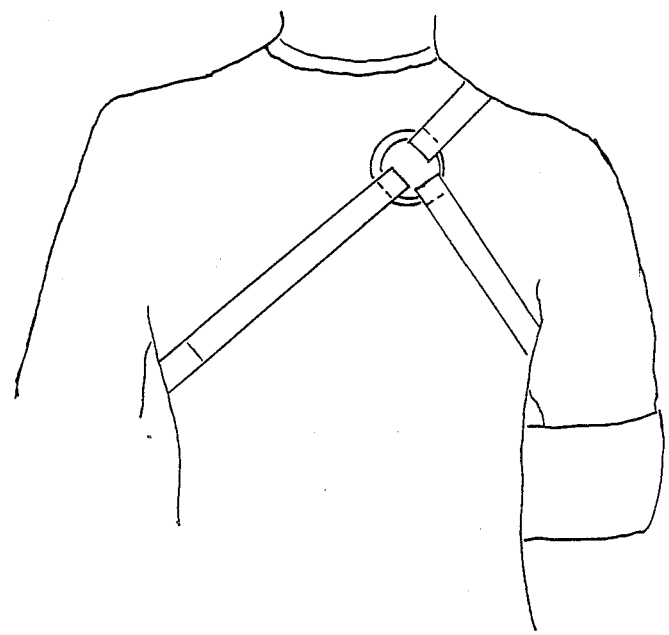
FIG. 4 illustrates the Arm sling as seen from the rear of the patient.

The method of fitting the Arm sling onto the patient's affected arm is as follows:

Position the trough of the invention, 50, so that the elbow of the affected arm is tucked into the closed end and the fingers are towards the open end, with the D rings, 10, 12, 14, 16, pointing upward. Take the three strap device 60, and pass each of the two equal length straps, 18, 20, through each of the proximal D rings, closest to the elbow, 14, 16, and fasten the Velcro hook and loop pieces, 24 to 30, and 26 to 32, such that the strap 18 passes over the anterior aspect of the affected shoulder and strap 20 passes over the posterior aspect of the affected shoulder, making sure that the distribution ring lies around the medial border of the scapula. Take the longer elastic strap, 22, and bring under the arm pit of the unaffected side and attach to the D rings which are at the distal side of the trough, 10, 12, passing the strap through both said D rings together and fastening the Velcro loop and hook portion, 28 and 34. Reposition the trough 10, so that the entire arm fits snugly and comfortably, adjust each of the Velcro fastening means to provide proper lengths, such that the Arm sling fits not too tightly.

It is to be understood that the description of the embodiment of this invention is merely illustrative of the application of the principles of the invention. Reference herein to details of the illustrated embodiments are not intended to limit the scope of the claims which themselves recite those features regarded as essential to the claim. Further, even though the invention is described for use for stroke patients, the use of the invention is not limited to that function since many of the features can be used by patients of orthopedic injuries, with beneficial results.

I claim:

1. An Arm Sling comprising of:
    a. a trough means for supporting the entire arm from the fingers to the elbow and a portion of the arm, proximally at the elbow and distally at the hand and fingers, said trough means being made of soft, durable material;
    b. a strap means, comprising of a strap member connected at the proximal anterior end of the upper edge of said trough means, and a strap member connected at the proximal posterior end of the upper edge of said trough means, said strap members connected together at their other ends by a distribution O ring, and positioned over the shoulder of the affected arm.
    c. a strap means comprising of a strap member connected at one end to said distribution O ring, and at the other end to the distal end of the upper edges of said trough means, positioned under the axilla of the unaffected arm to provide distribution of the weight away from the neck.

2. A sling as set forth in claim 1 with said strap fastening means being adjustable in length at their connecting points, to provide optimum support of the arm, support of the head of the humerus into the glenoid fossa, proper positioning of the arm, and comfort to the wearer.

3. A sling set forth in claim 1 where said strap fastening means are made of elastic strap material to provide quick stretch to the paralyzed muscles of the affected arm.

* * * * *